United States Patent [19]

Giddings et al.

[11] 4,250,026
[45] Feb. 10, 1981

[54] CONTINUOUS STERIC FFF DEVICE FOR THE SIZE SEPARATION OF PARTICLES

[75] Inventors: John C. Giddings; Marcus N. Myers, both of Salt Lake City, Utah

[73] Assignee: University of Utah, Salt Lake City, Utah

[21] Appl. No.: 38,592

[22] Filed: May 14, 1979

[51] Int. Cl.³ .............................................. B03B 5/00
[52] U.S. Cl. ...................................... 209/155; 209/1; 209/156; 209/209; 209/12
[58] Field of Search ........................... 209/1, 155–157, 209/39, 133, 134, 136, 12, 460, 477, 478, 483, 209; 210/519–521, 31 C, 22 C; 55/67; 73/432 PS, 23, 23.1

[56] References Cited

U.S. PATENT DOCUMENTS

| | | | |
|---|---|---|---|
| 1,198,126 | 9/1916 | Hedman | 209/156 |
| 3,449,938 | 6/1969 | Giddings | 55/67 X |
| 3,482,692 | 12/1969 | Postma | 209/156 |
| 4,147,621 | 4/1979 | Giddings | 210/22 C |

OTHER PUBLICATIONS

Giddings et al., "Steric Field-Flow Fractionation: A New Method for Separating 1–100 μm Particles", Separation Science and Technology, 13(8), pp. 637–645, 1978.

Primary Examiner—Ralph J. Hill
Attorney, Agent, or Firm—Thorpe, North, Western & Gold

[57] ABSTRACT

A method and apparatus for continuous, steric field-flow fractionation and segregation of particles according to particle size. An elongate, fluid flow channel carrying a stream of entrained particles is subjected to a force field which urges the particles against one of the channel walls. The field strength is sufficient and in an appropriate direction to maintain the particles in close proximity to the wall so that particle size determines the rate of movement down the channel, the larger particles being exposed to the higher flow rates toward the center of the flow stream. The combined effects of fluid flow forces and force field strength develops a pattern of selective particle deflection from a point of particle infusion near the top of the channel, such that the particles drift and settle into segregated groups of common particle size. Where gravity is used as the force field, the desired particle movement is obtained by rotating the flow channel about an axis substantially parallel to the direction of flow to an inclined position with respect to the force field.

15 Claims, 5 Drawing Figures

CONTINUOUS STERIC FFF DEVICE FOR THE SIZE SEPARATION OF PARTICLES

This invention was funded in part by a grant from the National Institute of Health, Department of Health, Education and Welfare.

BACKGROUND OF THE INVENTION

This invention relates to a method of field-flow fractionation (FFF), and more particularly to the use of relatively high field gradients to establish two-dimensional particle movement at the wall of a field-flow fractionation system.

FFF, disclosed previously in U.S. Pat. No. 3,449,938, is the descriptive term referring to a broad field of technology developed primarily for separation and characterization of macromolecules and particles. Generally, FFF has demonstrated a capability to deal with extreme ranges of mass, including particle sizes varying from a molecular weight of 600 to particles over 1 micrometer in diameter.

As explained in the referenced patent and also in a previous patent application of the present inventor (U.S. patent application Ser. No. 810,835), FFF involves the differentiation and segregation of particles along a flow channel under the influence of a force field applied across the flow channel. The effect of this field, which is usually applied perpendicular to the axis of the flow channel, is to force particles of different sizes into equilibrium layers of different effective thickness against a channel wall which operates as a restraining wall with respect to the particles. The thickness of the layers is determined primarily by (1) the interplay between the field-induced forces which tend to compact particles against the restraining wall and (2) Brownian motion which tends to disperse the particles away from the wall.

Steric field-flow fractionation or steric FFF was disclosed in U.S. patent application Ser. No. 953,655 and provides a method for separating particles according to size into discrete zones or into a continuous size spectrum in an effluent stream. It was suggested therein that the method was readily applicable to particles in the range 1–100 micrometers, and actual separations of considerable sharpness were carried out in the range 10–30 micrometers using samples of glass beads. Essentially, this method involved using a field strength of sufficient magnitude perpendicular to the direction of channel flow so that substantially all particles are pressed against one of the channel walls. In this sense, steric FFF is the limiting form of general field-flow fractionation (FFF) methodology. In steric FFF, the effective thickness of layers of particles forced by a field toward the wall of a flow channel is determined by particle size rather than by the normal processes of Brownian displacement. Since the influence of the former increases and the latter decreases with particle size, steric FFF is especially applicable to particles greater than 1 micrometer in diameter, whereas usually FFF is applied to submicron particles and macromolecules.

Steric FFF is therefore a method in which particles are rolled or tumbled along the smooth surface of a narrow channel by a flow stream confined in the channel. Large particles are tumbled more rapidly than small ones because they are forced by their own size further into the high velocity regions of the parabolic channel flow. The largest particles in the mixture therefore emerge first from the channel, followed by a continuum of decreasing sizes. It should be noted that this sequence is opposite to the normally observed elution of smaller to larger particles in FFF.

During fractionation under sedimentary steric FFF particles are held near the wall by gravity. The combination of the gravitational displacement toward the wall and the limitations on this displacement by the physical dimensions of the particle leads to well-defined and precisely positioned layers of particles of a given size, and it leads therefore to uniform displacement of the particles in the laminar flow stream of the channel.

Because particle displacement was confined to a single dimension in the previously described steric FFF, utility of the method was limited to fractionation of a single sample. Basically, such a sample was injected and the particles were allowed to separate prior to further sample injection. Such a system was not suitable for continuous operation in view of the differential rate of particle displacement along one axis only. This displacement would result in migration of larger particles into preceding groups of smaller particles, if multiple or continuous sample injections occurred. Therefore, FFF has heretofore continued under the limitation of single sample injection or batch operation, without a method for continuous operation.

OBJECTS AND SUMMARY OF THE INVENTION

It is therefore an object of the subject invention to provide a method and apparatus for continuous steric FFF.

It is a further object of this invention to provide a method and apparatus for continuously segregating and separating particles from a channel flow stream, based on particle size and density.

It is yet another object of the present invention to provide a method and apparatus which permits withdrawal of segregated particles without interruption of the continuous steric FFF operation.

These and other objects are realized in a method and apparatus for continuous steric FFF which includes a field flow fractionation system having a flow channel formed between opposing side wall surfaces and between spacer top and bottom wall surfaces, with one of said side wall surfaces being a smooth retaining wall against which particles entrained in a fluid medium within the channel may be urged and segregated into common particle sizes. The flow channel includes a means for introducing and maintaining a substantially uniform, nonturbulent flow of fluid medium along its length. Particle suspensions to be subjected to continuous steric FFF are injected through a particle inlet means which is coupled to the channel and positioned toward an upstream location near the top wall surface. The continuous steric FFF apparatus further includes means for applying a force field represented by a field vector whose direction is at an acute angle with respect to the restraining wall area and toward the bottom wall. This force field has the effect of urging particles against the restraining wall in compacted relationship, as well as displacing such particles along a second dimension perpendicular to the direction of fluid flow and toward the bottom wall. The operation of a two-dimensional field and flow relationship developed by fluid flow and perpendicular force field develops a range of angles of particle deflection which are selectively different based on particle size and density.

The method of practice involves establishing a field-flow fractionation system having a force field whose direction is at an acute angle with respect to the opposing side wall surfaces of the channel and which has a component toward the bottom wall. This force operates in part to cause formation of a layer of a give class of particles against the restraining wall, the layer thickness being controlled by the steric exclusion of particles from the space occupied by the restraining wall. This same condition may be described as the level of force required to develop a condition wherein the mean Brownian displacement of the particles from the restraining wall is approximately equal to or less than the mean radius of such particles. Both of these conditions are realizations of the steric field flow fractionation method and result in all particles of a given class being in contact or near contact with the restraining wall such that the distance of the particles from the restraining wall is a function of particle size.

A suspension of particles to be subjected to fractionation is injected near the top wall, at an upstream location of the flow channel with the aforementioned steric FFF conditions in operation. As particles enter the flow stream, each particle experiences movement to the side wall surface followed by displacement along the restraining wall toward the bottom wall surface. The differential response of particles to this force field, together with downstream flow forces, develop different trajectories through which particles of various sizes travel. Pockets and collection ports are located at the bottom wall surface to enable withdrawal of the separated particles according to common particle size, without interruption of the fractionation process.

Other objects and features of the present invention will be apparent to those skilled in the art, from the following detailed description, taken in combination with the attached drawings, in which:

FIG. ONE is a graphic representation of a segment of a steric FFF system adapted for continuous operation.

FIG. TWO is a cross-sectional view taken along line 2—2 of FIG. 1.

FIG. THREE is a top view (looking down on side wall) of a continuous steric FFF channel.

FIG. FOUR is a plot showing different particle sizes collected along sampling locations of the channel.

FIG. FIVE is a plot of the particle diameter versus reciprocal of the position at which particles were collected.

DETAILED DESCRIPTION OF PREFERRED EMBODIMENTS

Figure 1:
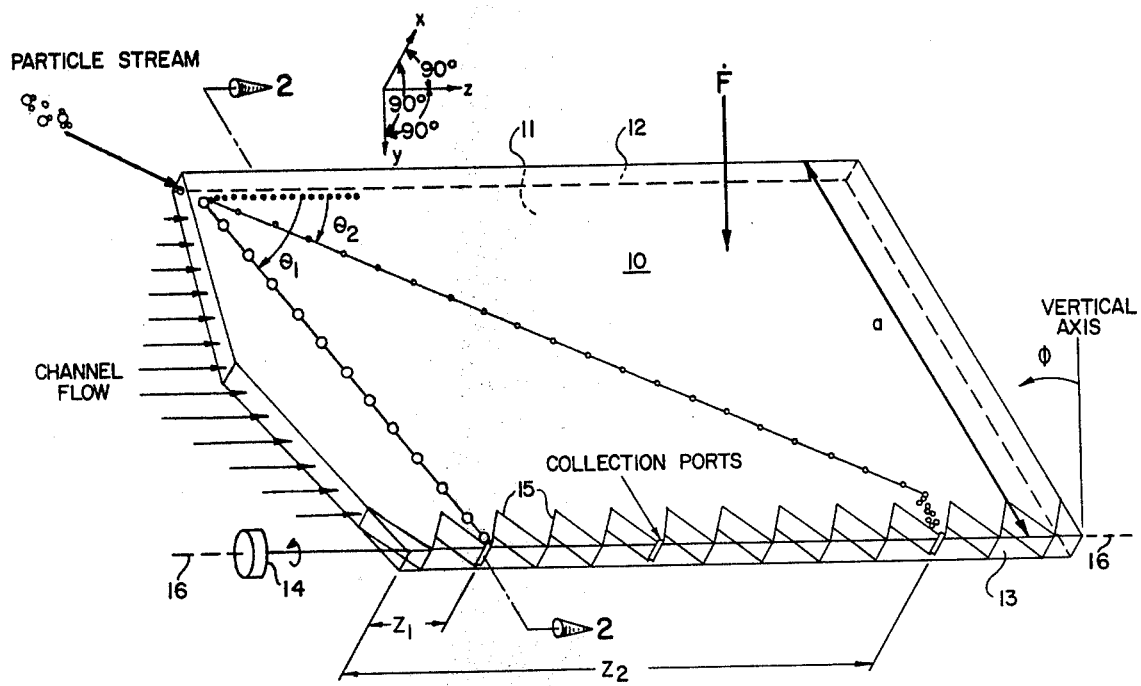

Referring now to the drawings:

A segment of a continuous steric FFF apparatus is shown in FIG. ONE in graphic form. The flow channel is formed between opposing side wall surfaces 10 and 11 and between top 12 and bottom 13 wall surfaces which are sandwiched between the side walls to enclose the flow channel. As used herein, top wall refers to the location where particles are injected, and need not conform to a spatial orientation of high as opposed to low. Likewise, bottom wall refers to a region into which particles flow in response to a force field, and not to a wall spatially below the top wall.

Whereas the original channel used for steric FFF was only 0.127 mm in thickness by 10 mm in width by 860 mm in length, in order to employ a second dimension for continuous fractionation, the width "a" should be considerably increased—to perhaps 100 mm. Collection ports 15 are installed along the bottom surface 13 of the channel to catch and retain particles falling therein. When sedimentation forces are used to develop the field vector $\vec{F}$, the device is tilted by use of rotational means 14 about an axis of rotation 16 so that the particles will sediment slowly across the enlarged width of the retaining wall 11, while being simultaneously carried downstream. However, according to the strategy of this approach, the particles are to be held continuously against the wall in order to ensure the uniformity of their migration. Therefore, the channel is not to be tilted fully on edge, but is to be maintained at some angle $\phi$ with respect to the vertical, which is referred to herein as an acute angle component of the force field $\vec{F}$. FIG. 1 illustrates the overall configuration and tilt of the channel.

Clearly, the steric effect is an important element in the control of particle migration in this separation scheme. With a full vertical tilt, particles subject only to sedimentation forces would distribute themselves over the thickness of the channel and would therefore be subjected to flow displacement velocities ranging from near zero at the wall to the maximum flow velocity at the center of the channel. This formation of steric layers by tilting the device with an acute angle field component $\vec{F}$ avoids this difficulty.

It is, of course, possible to use the principles proposed here in conjunction with forces other than gravity to develop the wall layer of particles and cause lateral migration. For instance, a channel could be coiled within a centrifuge in order to deal with particles of smaller diameter or lower density. Likewise, an electrical field could be used in either or both of the two-dimensions represented by the X and Y axes. While continuous electrophoresis devices have been in use for a long time, none have been coupled with steric displacements in an effort to increase velocity uniformity and particle resolution.

In a broad sense, continuous steric FFF is developed by imposing a force represented by the force vector $\vec{F}$ at an acute angle with respect to the restraining side wall 11, and directionally oriented with a component toward the bottom wall 13. If this force is centrifugal, it is apparent that this bottom wall may actually be at a higher elevation than the top wall 12 where the particles will be injected into the channel flow stream. The same is true with other fields such as electrical or magnetic. The important condition is the presence of a force which retains the particles in steric hindrance at the restraining wall, while gradually urging them across the channel width toward the bottom wall surface.

It will also be noted that this field vector $\vec{F}$ can be the vector sum of numerous force field vectors having complementary orientations. For example, the channel shown in FIG. 1 could be horizontal, with an electric field imposed in the same plane toward the bottom wall. A second force field (gravity) would operate perpendicular to the channel to establish steric flow conditions. The vector sum of these forces would yield a single field vector $\vec{F}$ having the suggested acute angle with respect to the restraining wall required to develop particle separations.

Figure 2:
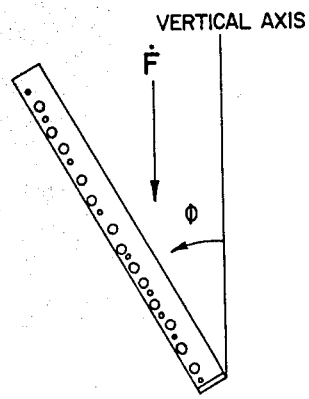

Separation in continuous steric FFF depends on a selective variation with particle size of the angle of deflection, $\theta$, of particles introduced in the upper corner of the device. As shown in FIGS. 1 and 2, particles of different size develop differing trajectories across the flow channel. The larger particle is illustrated with the shortest path, which terminates at a distance Z, from the point of injection. This trajectory is represented by deflection angle $\theta$, from the dotted channel flow line.

This angle of deflection is a function of the two particle velocities, $U_z$ along the fluid flow axis an $U_y$ along sedimentation axis y. This relationship is reflected in the following equation.

$$\tan \theta = U_y/U_z \tag{1}$$

The velocity U can be approximated using the retention equations disclosed in $$U_z = 3\alpha d <v>/w \tag{2}$$

where d is effective particle diameter, v is mean channel flow velocity, t is channel thickness and $\alpha$ is a retardation factor (>1) expressing the reduction in velocity due to rotational drag.

Velocity $U_y$ can be written as $$U_y = F_y/f \tag{3}$$

where $F_y$ is the sedimentation force along axis y and f is the friction coefficient. Force $F_y$ is related to the tilt from the vertical, $\phi$, by the equation $$F_y = m'g \cos \phi \tag{4}$$

where g is gravitational acceleration and m' is the effective mass (actual minus buoyant mass) of the particle. The latter is given by $(\pi/6)d^3\Delta\rho$ for spheres, where $\Delta\rho$ is the difference between particle density and carrier density. This yields the special equation for spheres $$F_y = (\pi/6) d^3 \Delta\rho g \cos \phi \tag{5}$$

Friction coefficient f can be obtained from the modified Stokes equation $$f = 3\pi\eta d(\beta) \tag{6}$$

where $\eta$ is viscosity and $\beta$ is a correction factor (>1) allowing for the increased drag of a particle being sedimented along a solid surface. If the particles are non-spherical, d becomes the Stokes diameter, $d_s$. However, for simplicity, the subsequent treatment will be limited to spherical particles.

The substitution of Eqns. 5 and 6 into 3 yields the sedimentation velocity $$U_y = d^2 \Delta\rho g \cos \phi \ 1/18\eta\beta \tag{7}$$

This and Eqn. 2 substituted into Eqn. 1 give the basic deflection equation $$\tan \theta = \frac{dw\Delta\rho g \cos\phi}{54 \eta < v > (\alpha\beta)} \tag{8}$$

Equation 8 shows that the deflection (as measured by $\tan \theta$) is directly proportional to diameter d. Clearly, the dependence on d is weaker than that of sedimentation alone, where, as shown by Eqn. 7, a square dependence on d is formed. However, the inventors believe that the uniformity in displacement conditions introduced by employing steric FFF as an element of the separation may more than compensate for this disadvantage in many cases, as well as yielding a continuous approach to fractionation.

Although the selective deflection of particles of different diameters leads to separation, the coordinate of interest is the distance downstream where the particle trajectory strikes the lower edge of the channel and the particles are collected. If this distance is Z and the channel width is a, the applicable equation is $$Z = a/\tan \theta \tag{9}$$

Substituting the expression for $\tan \theta$ from Eqn. 8, we get $$Z = \frac{54\eta <v> a (\alpha\beta)}{dw\Delta\rho g \cos\phi} \tag{10}$$

This equation shows that position Z is inversely related to particle diameter d.

Figure 3:
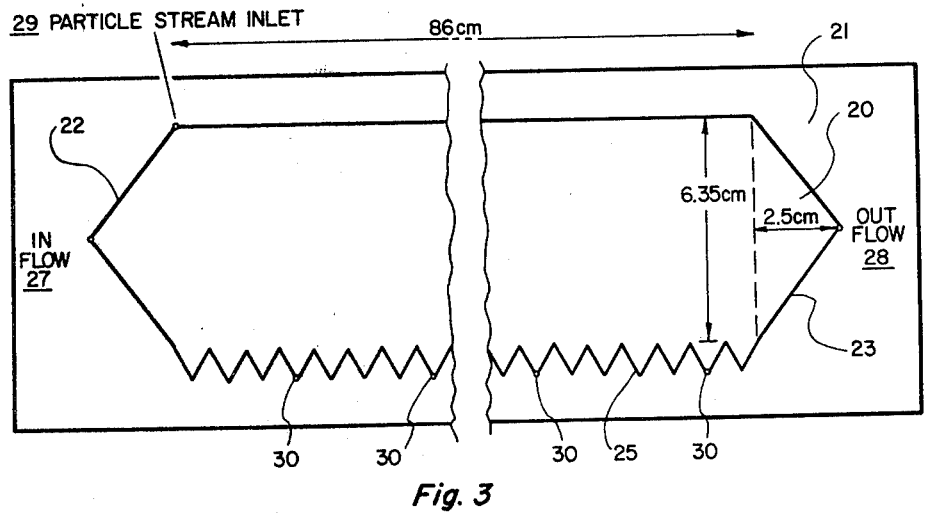

The flow channel from the actual continuous steric FFF apparatus used is illustrated in FIG. 3. This flow channel consisted of the space 20 cut out of a sheet of Mylar 21 having a thickness at 0.127 mm. The shape and dimensions of the channel are shown in FIG. 3. It will be apparent that a broad range of shapes and dimensions may be selected based on accepted principles of fluid dynamics. For example, the tapered ends 22 and 23 were designed to streamline the entering and exiting flow, and the notches 25 along the bottom were provided to collect different sedimenting fractions.

The column was constructed by sandwiching the Mylar 21 with the cut-out channel between two 12.7 mm thick pieces of plate glass, which in turn were clamped between two 50.8 mm thick Plexiglas bars. To provide carrier stream flow into and out of the channel, holes were drilled through both glass and Plexiglas into the apices of the tapered ends of the flow space, and stainless steel tubes were installed. These are identified as in flow 27 and outflow 28. A similar port 29 for sample injection was placed close to the upper (unnotched) edge at the point where the channel first reached its nominal rectangular width. Holes 30 for withdrawing fractions were similarly provided in the bottoms of fifth, ninth, thirteenth, and seventeenth notches, and in every fifth notch beyond that. This allowed collection of samples without disassembling the apparatus.

The whole assembly was suspended in a yoke devise which allowed the apparatus to be tilted to any desired angle, $\phi$, with respect to the vertical. In the subject experiments, an angle of 23° was used. This angle represents the acute angle field component previously discussed, and may range between 1° to 89°, depending on flow rates and field strengths.

The particles employed in this study were drawn principally from a batch of experimental spherical porous silica particles in the nominal size range 4-23 micrometers provided by E. I. duPont deNemours Co. Several runs were also made using glass beads from Microbead Corp. and English Glass Co., previously roughly sized by air elutriation. These glass beads contained a fairly large proportion of broken and irregularly shaped particles and spheres with entrained bubbles. The carrier stream and the solution used to suspend the particles was 0.01 M $NH_4OH$ in distilled water. The experimental material was continuously injected into the channel through the inlet 29 from a stirred reservoir containing 0.2 g of particles in 15 ml of diluent. Two Chromatronix Cheminert CMP IV metering pumps controlled column flow and sample injection.

The column was operated by first establishing the flow down the channel (24 ml/hr), then starting the injection flow (2.4 ml/hr). After operation for several hours, samples were withdrawn from the sampling ports. These were examined microscopically at 100× and 437×, and then photographed. Size distributions were measured by comparing the photographs at 437× with the photograph of a stage micrometer from Leitz Wetzlar, Germany.

Figure 4:
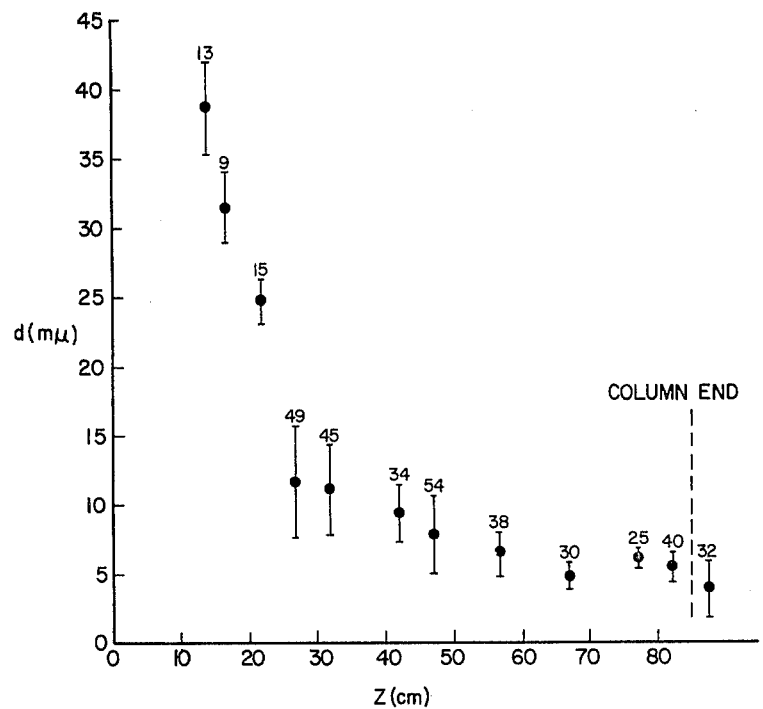

FIG. 4 shows the results of a 4-hour run with the spherical silica microspheres. As predicted by the theory, the largest spheres accumulate in the early collection notches and the smallest spheres are distributed in the ports near the downstream end of the column. A continuous gradation in size is seen although some erratic changes in the size pattern are apparent. The length of the bars, which reflect the plus and minus standard deviation in diameter of each fraction, indicate that the collected samples are fairly narrow in distribution, although considerable deviations exist here also.

Figure 5:
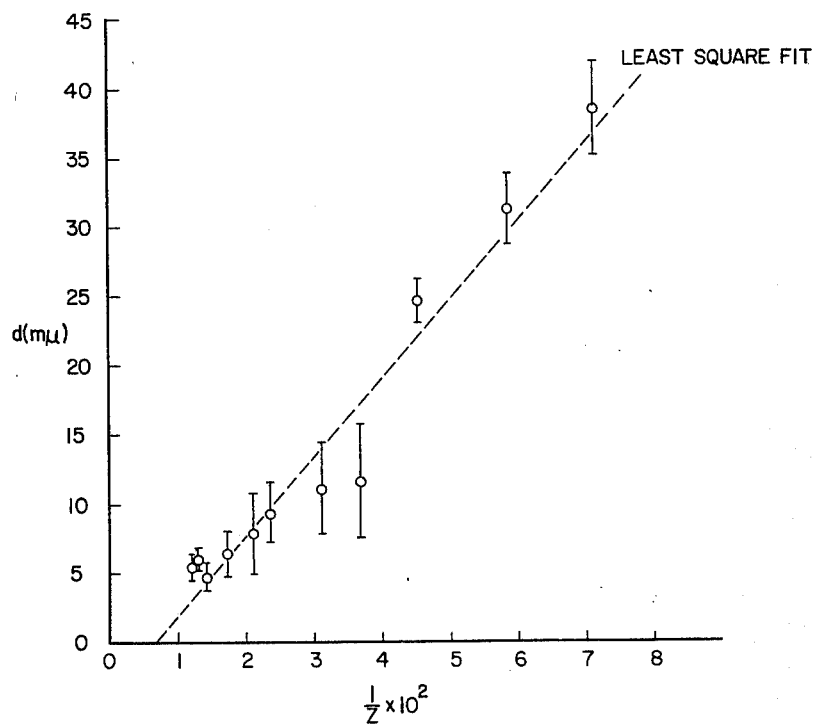

In order to look more critically at the data in the light of the theory developed previously, it should be noted that Eqn. 10 predicts that the diameter of the particle should be inversely related to the position (or slot number) Z at which it is collected. This conclusion can be tested by plotting particle diameter d versus 1/Z. Such a plot is shown in FIG. 5. The dashed line is the least squares fit to the data.

FIG. 5 shows that the data follow the expected trend, but are subject to measurable anomalies. It appears as if there are two slopes, one corresponding to large particles and another to small particles. However, this may be only a sag in the curve due to the enhanced "cooperative" sedimentation of $\sim 12$ micrometer particles, present in some abundance.

The slope of the line in FIG. 5 is also subject to theoretical estimation. Unfortunately, parameters $\alpha$ and $\beta$ in Eqn. 10 are at present undefined. If we assume that the product $\alpha\beta$ is equal to unity, which hopefully is valid within a factor or two, then the slope combined with Eqn. 10 yields a density difference $\Delta\rho$ of 0.43 g/ml. This is in good accord with the bead density that estimated from sedimentation experiments, $\sim 1.5$ g/ml, which upon subtraction of the density of water yields $\Delta\rho=0.5$ g/ml, a value only slightly higher than that (0.43 g/ml) suggested by the data in FIG. 5.

It will be apparent to those skilled in the art that the aforementioned description is only an illustration of numerous methods which may be employed to practice the subject invention. For example, the channel need not be tilted from vertical axis where a force field can be tilted or applied at a slant angle to develop the acute angle component or field vector. Such may be the case where an electrical field is applied with charged particles or other electrosensitive particles. Similarly, other geometric configurations may be utilized as opposed to an elongate, planar channel as suggested earlier. With this in mind, it is to be understood that the scope of invention is defined by the appended claims and is not to be limited by examples previously suggested.

We claim:

1. Apparatus for Continuous Steric FFF comprising:
    (a) a field flow fractionation system having an elongate flow channel formed between opposing side wall surfaces and between narrow top and bottom wall surfaces, one of said side wall surfaces being a smooth restraining wall against which particles to be entrained in a fluid medium within said channel may be urged into common particle sizes;
    (b) means for introducing and maintaining a substantially uniform flow of fluid medium along a length of said channel;
    (c) particle inlet means coupled to said channel and positioned toward an upstream location of said channel and near said top wall surface, thereby adapting said system with a conduit for infusion of particles to be fractionated; and
    (d) means for developing a force field represented by a field vector whose direction is at an acute angle with respect to said restraining wall and having a component toward said bottom wall surface, said force field having capacity to interact with a class of particles to be entrained within said channel.

2. Apparatus as defined in claim 1, wherein said bottom wall surface includes pockets formed along its length which operate to catch or retain particles falling therein.

3. Apparatus as defined in claim 2, further comprising collection ports within several or all of said pockets adapting said system for withdrawal of particles contained therein during continued operation of the apparatus.

4. Apparatus as defined in claim 2, wherein said pockets are formed as troughs in a saw tooth configuration.

5. Apparatus as defined in claim 4, wherein collection ports are located at the base of said troughs at displaced locations along the length of the bottom wall surface, said ports providing access for withdrawal of particles trapped in said troughs during operation of said apparatus.

6. Apparatus as defined in claim 1, wherein said particle inlet means comprises a duct which opens into said channel and is adapted for passing a fluid with particle constituent into a top portion of flow stream within said channel.

7. Apparatus as defined in claim 1, wherein said force field comprises gravitational force and is represented by said field vector, said channel being tilted at the base surface to thereby incline the restraining wall along its longitudinal axis with respect to the force vector.

8. Apparatus as defined in claim 1, wherein said field vector is a vector summation of a combination of force vectors representing all particle influencing forces applied with respect to said restraining wall.

9. Apparatus as defined in claim 8, wherein applied forces include a combination of electrical and gravitational forces.

10. Apparatus as defined in claim 1, wherein said side wall surfaces are spaced apart by a distance of 0.01 mm to 10 mm.

11. Apparatus as defined in claim 1, wherein said channel further comprises rotation means attached at said channel to form an axis of rotation along the length of the channel, thereby providing means to adjust said channel to angles of inclination for said restraining wall between the range of approximately 1° to 89° with respect to vertical.

12. Apparatus as defined in claim 1, further comprising means for developing a substantially uniform flow of fluid medium along said channel, thereby developing a nonparallel fluid force component with respect to said field vector.

13. In a field flow fractionation system including a flow channel formed between opposing side wall surfaces and between narrow top and bottom wall surfaces, a method of performing continuous steric FFF comprising the steps of:

(a) establishing a uniform fluid flow along said channel;

(b) subjecting said channel to a force field whose direction is at an acute angle with respect to the opposing side wall surfaces of the channel with a component toward the bottom wall surface, said force having sufficient relative strength with respect to particles contained within said channel to cause migration of a given class of said particles against one of said side wall surfaces operable as a restraining wall such that the mean Brownian displacement of said particles from the restraining wall is approximately equal to or less than the mean radius of said class of particles;

(c) injecting a continuous stream of particles near the top wall and at an upstream location of said flow channel; and (d) collecting segregated groups of particles near the bottom wall of said channel, each group having particles of common size.

14. A method for continuous steric FFF as defined in claim 13, wherein the acute angle force field direction is developed by rotating the flow channel along a longitudinal axis to tilt the channel with respect to the force field.

15. A method as defined in claim 13, wherein said force field in acute angle direction is a composite force of a plurality of nonparallel forces whose vector summation produces a force vector.

* * * * *